United States Patent
Kennard, III et al.

(10) Patent No.: US 6,179,989 B1
(45) Date of Patent: Jan. 30, 2001

(54) ELECTRICAL AND CHEMICAL TREATMENT OF AN OXYGEN SENSOR

(75) Inventors: Frederick Lincoln Kennard, III, Holly; Robert Gregory Fournier, Burton; William John La Barge, Bay City; Carilee E. Cole, Davison; Earl Wayne Lankheet, Grand Blanc; Tie Wang, Troy, all of MI (US)

(73) Assignee: General Motors Corporation, Detroit, MI (US)

(*) Notice: Under 35 U.S.C. 154(b), the term of this patent shall be extended for 0 days.

(21) Appl. No.: 09/374,401

(22) Filed: Aug. 13, 1999

Related U.S. Application Data

(62) Division of application No. 09/089,758, filed on Jun. 3, 1998.

(51) Int. Cl.[7] .................................................. G01N 27/407
(52) U.S. Cl. ........................ 205/711; 204/421; 204/424; 204/426; 205/705; 216/100; 216/101; 216/108; 216/109; 252/79.2; 252/79.5
(58) Field of Search .................................. 204/421–429; 252/79.2, 79.5; 205/687, 704, 705, 710, 711; 216/96, 100, 101, 108, 109

(56) References Cited

U.S. PATENT DOCUMENTS

| | | | |
|---|---|---|---|
| 3,556,957 | * 1/1971 | Toledo et al. | 252/79.2 |
| 4,136,000 | * 1/1979 | Davis et al. | 134/41 |
| 4,169,777 | * 10/1979 | Young et al. | 204/427 |
| 4,277,323 | * 7/1981 | Muller et al. | 204/425 |
| 4,310,401 | 1/1982 | Stahl . | |
| 4,426,253 | * 1/1984 | Kreuz et al. | 252/79.5 |
| 4,986,880 | * 1/1991 | Dorfman | 252/79.5 |
| 5,334,284 | * 8/1994 | Ngo | 252/79.2 |
| 5,372,981 | 12/1994 | Witherspoon . | |
| 5,384,030 | 1/1995 | Duce et al. . | |
| 5,433,830 | 7/1995 | Kawai et al. . | |
| 5,467,636 | 11/1995 | Thompson et al. . | |
| 5,602,325 | * 2/1997 | McClanahan et al. | 204/424 |
| 5,616,825 | * 4/1997 | Achey et al. | 204/426 |

OTHER PUBLICATIONS

From: Solid State Ionics ¾ North–Holland Publishing Company, entitled "Low Temperature Performance of Fluoride–Ion Treated ZrO2 Oxygen Sensor", (1981) month unavailable pp. 631–634.

From: The American Ceramic Society, Inc., Advances in Ceramics, vol. 19, entitled "Multilayer Cermanic Devices", by John B. Blum and W. Roger Cannon, pp. 49–68 date available.

From: The Journal of Applied Electrochemistry 3 (1973) month available, entitled "On the Influence of the Annealing Temperature and Heavy Current Treatments on the Porous Sturcture of Platinum Electrodes and on the Kinetics of the Oxygen Reaction at High Temperatures", pp. 153–159 by S. Pizzini, M. Bianchi, P. Colombo, and S. Torchio.

From: Chemical Sensing with Solid States Devices by Marc. J. Madon and S. Roy Morrison, pp. 20–65. date unavailable.

From: Journal of Applied Electrochemistry 17 (1987) month unavailable, entitled Importance of Electrode/Zirconia Interface Morphology In High Temperature Solid Electrolyte Cells, by Turgot M. Gur, Robert A. Huggins, pp. 800–806.

* cited by examiner

*Primary Examiner*—T. Tung
(74) *Attorney, Agent, or Firm*—Vincent A. Cichosz

(57) ABSTRACT

The present invention relates to an improved oxygen sensor and particularly to oxygen sensors used as exhaust sensors in vehicles. The oxygen sensor, which has an improved lean-rich response time and operability at lower temperatures, has been chemically etched and electrically treated, or chemically etched with a non-hydrofluoric acid solution.

12 Claims, 6 Drawing Sheets

ELECTRICAL AND CHEMICAL TREATMENT OF AN OXYGEN SENSOR

This is a division of application Ser. No. 09/089,758 filed on Jun. 3, 1998, pending.

TECHNICAL FIELD

The present invention relates to an oxygen sensor electrode and especially relates to a chemically and electrically treated oxygen sensor for use as an exhaust sensor in a vehicle.

BACKGROUND OF THE INVENTION

Exhaust sensors are conventionally used in vehicles to sense the level of oxygen in the exhaust gases. These sensors detect changes in the exhaust gas content, i.e., when the content changes from rich to lean or lean to rich in relation to the air/fuel ratio. One known type of oxygen sensor is a flat plate oxygen sensor formed of various layers of ceramic and electrolyte materials laminated and sintered together with electrical circuit and sensor traces placed between the layers in a conventional manner. A typical co-sintered flat plate sensor element is disclosed in U.S. Pat. No. 5,433,830 to Kawai et al; and commonly assigned U.S. Pat. No. 5,395,506 to Duce et al.

Numerous attempts have been made to produce improved exhaust sensors. One such sensor is disclosed in commonly assigned U.S. Pat. No. 5,384,030 to Duce et al. This patent discloses an exhaust sensor having a substrate with a dielectric material, an electrolyte material, and a transition zone disposed therebetween. Another improved sensor is disclosed in U.S. Pat. No. 5,733,504 to Paulus et al. This patent addresses lean switch point by teaching the use of a pre-equilibration zone on an exhaust gas sensor to provide a catalytic site to catalyze less reactive components of the exhaust gas prior to the gas sample reaching the sensor's exhaust side electrode.

What is needed in the art is an improved exhaust sensor having improved performance, reduced sensitivity to processing, reproducibility and potentially higher manufacturing tolerances.

SUMMARY OF THE INVENTION

The present invention comprises oxygen sensors and methods for making the same. One embodiment is an oxygen sensor, comprising: a solid electrolyte disposed between and bonded to a cathode electrode and an anode electrode to form an electrode assembly, wherein at least one of said electrodes has been chemically etched, and said electrode assembly has been electrically treated.

Another embodiment is an oxygen sensor, comprising: a solid electrolyte disposed between and bonded to a cathode electrode and an anode electrode to form an electrode assembly, wherein at least one of said electrodes has been chemically etched with a non-hydrofluoric acid solution.

One method for producing an oxygen sensor comprises the steps of: disposing anode and cathode electrodes on opposite sides of a solid electrolyte to form an electrode assembly, electrically treating the electrode assembly, and chemically etching at least one of the electrodes.

Another method for producing an oxygen sensor comprises the steps of: disposing anode and cathode electrodes on opposite sides of a solid electrolyte to form an electrode assembly and chemically etching at least one of the electrodes with a non-hydrofluoric acid solution.

These and other objects, features and advantages of the present invention will be apparent from the following brief description of the drawings, detailed description, and appended claims and drawings.

BRIEF DESCRIPTION OF THE DRAWINGS

The present invention will now be described by way of example with reference to the following Figures, in which.

DETAILED DESCRIPTION OF THE INVENTION

The present invention is an improved exhaust sensor and method for making the same comprising electrically treating and chemically etching the sensor in order to improve sensor performance characteristics, catalytic activity on the surface of the sensor, and reproducibility of the signal, to reduce sensitivity to process variation, and to allow for higher manufacturing tolerances.

Figure 1:
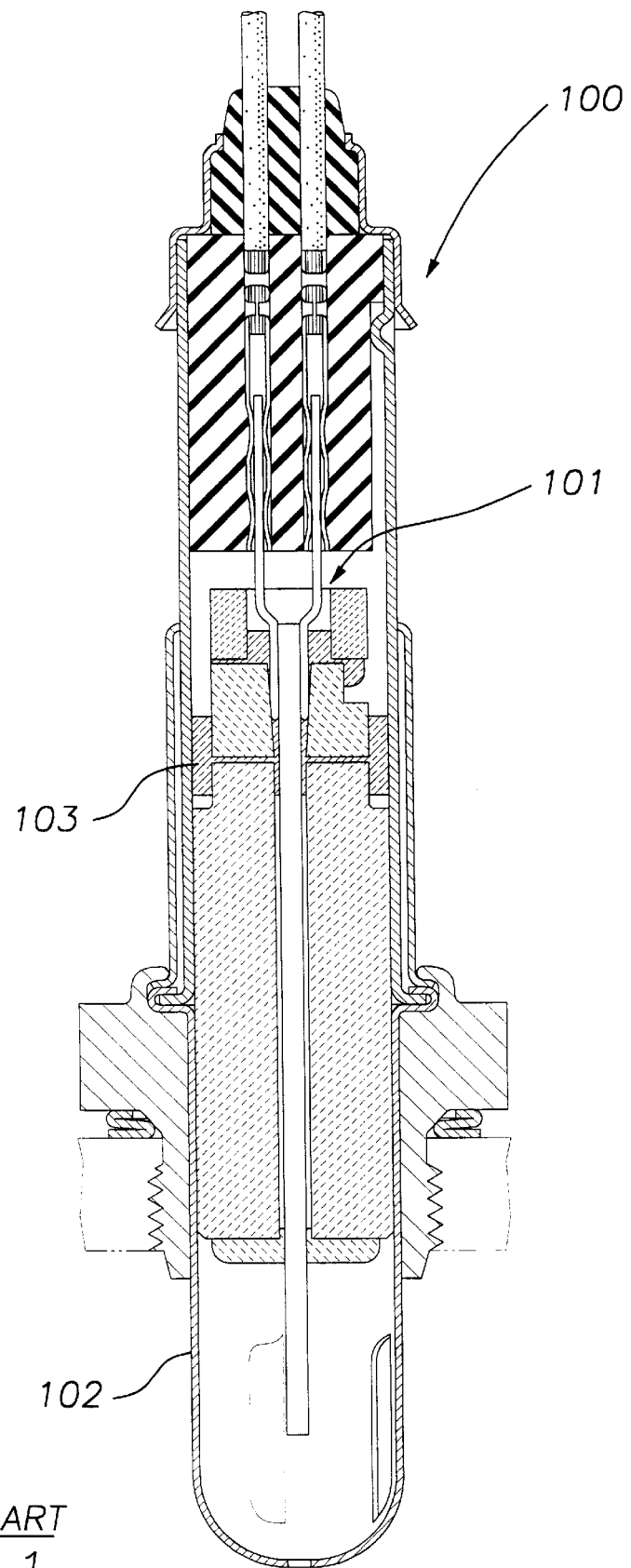
FIG. 1 is a prior art cut-away view of a planar exhaust sensor.

The exhaust sensor of the present invention can be any conventional sensor such as those disclosed in commonly assigned U.S. Pat. Nos. 5,467,636, 5,602,325, 5,616,825, 5,384,030, and 5,733,504. (The relevant portions of which are hereby incorporated by reference). Referring to FIG. 1, one possible, planar exhaust sensor 100 comprises an electrode assembly 101 disposed within a metal tube utilizing a metal to glass seal 103 to isolate the sensing electrode 3 (see FIG. 2)(cathode electrode), from the exhaust electrode 5 (anode electrode). Exhaust gas gains access to the sensing electrode by means of a louvered shield 102 in the sensor.

Figure 2:
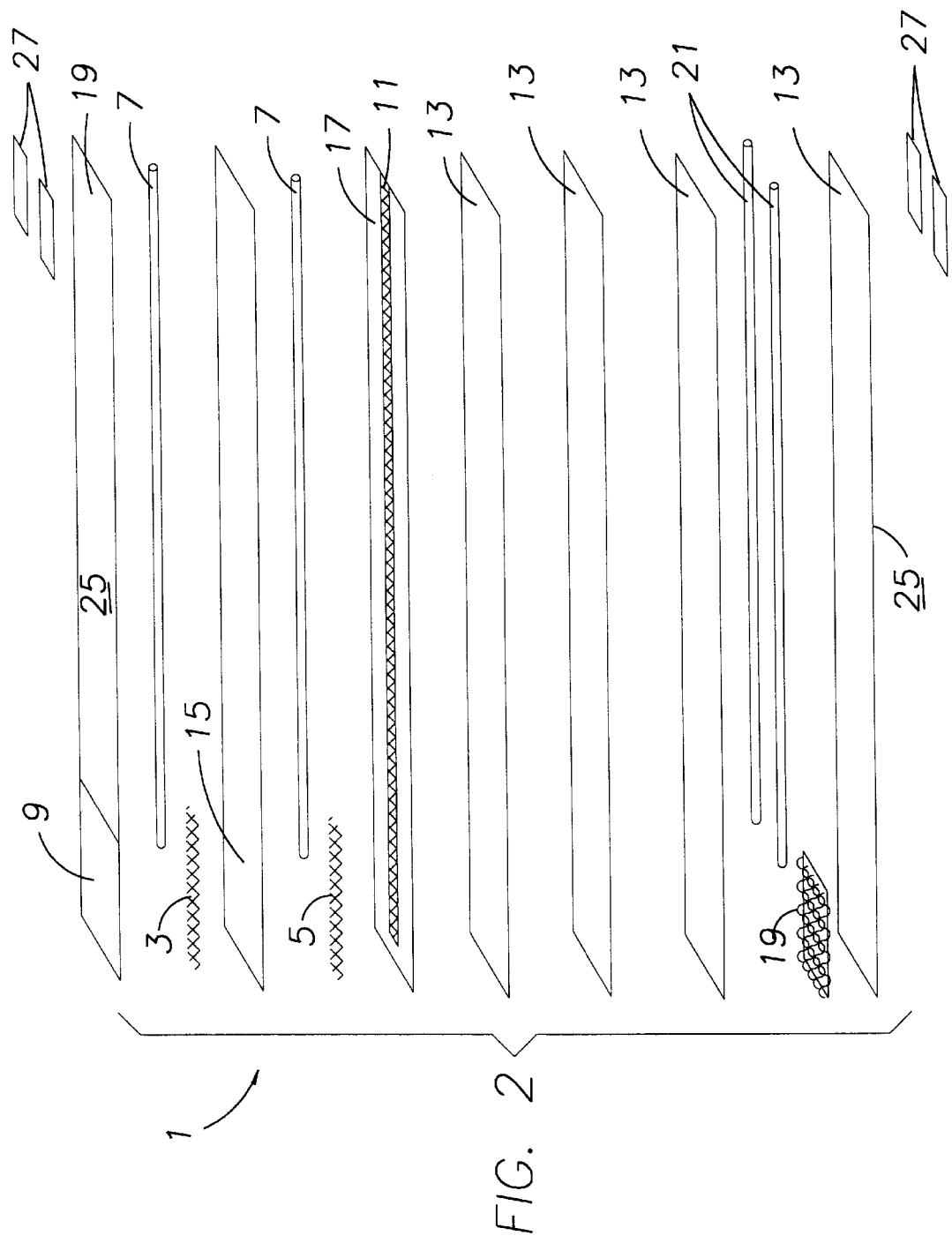
FIG. 2 is an exploded view of a planar electrode assembly.

Referring to FIG. 2, the electrode assembly 1 comprises a layered, sintered structure of electrodes 3, 5 and electrode leads 7, disposed on each side of a solid electrolyte 15, typically zirconia, with a protective layer 9, typically alumina, having a porous end disposed adjacent to the electrode 3. The other side of the electrolyte 15 has an insulating layer 17, typically alumina, containing an air channel 11 disposed therethrough, adjacent to the electrolyte 15 such that reference air contacts electrode 5. Disposed between this insulating layer 17 and heater 19 with heater leads 21, is one or multiple protector plates 13, also typically alumina. On the opposite side of the heater 9 is an end protector plate 13. Finally, disposed on both sides 23, 25 of the exterior of this layered structure, on an end opposite the electrode end, are contact pads 27.

Once the electrode assembly has been assembled, laminated and sintered, it is both chemically etched and electrically treated. The electrical treatment essentially eliminates sensor-caused negative voltage readings, i.e., it shifts the sensor output voltage upwards (to positive). In contrast, the chemical treatment, etching, increases the amplitude of the signal.

Figure 3:
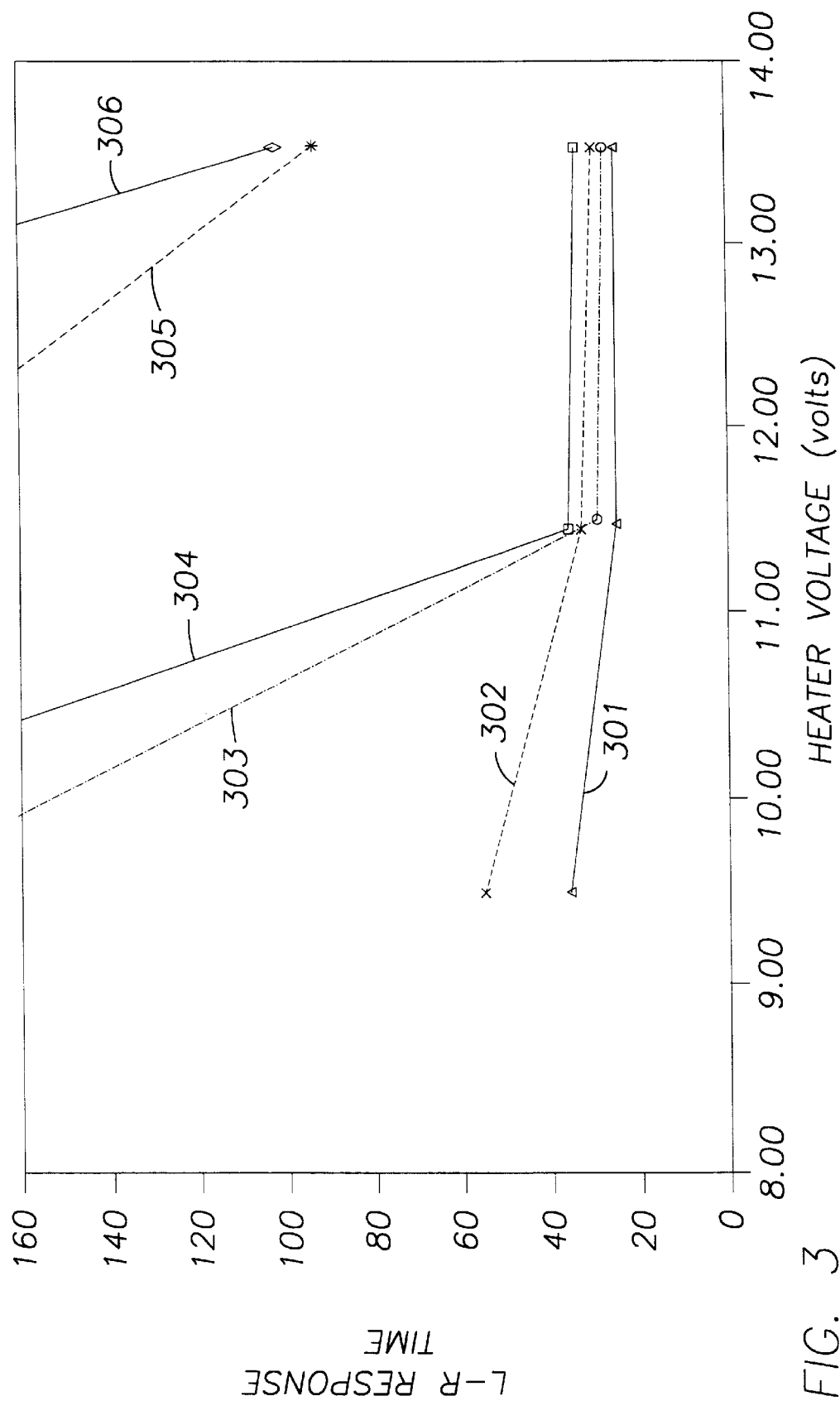
FIG. 3 is a graphic representation of response time for various exhaust sensors including those of the present invention versus heater voltage.

As shown in FIG. 3, the combination of these preparation processes produces an improved exhaust sensor having faster response times versus untreated exhaust sensors, with false leakage readings virtually eliminated. Line 306 represents an exhaust sensor in which the electrode assembly has been electrically treated, line 305 represents an exhaust sensor in which the exhaust sensor has been electrically treated, line 304 represents a hydrofluoric acid etched electrode, line 303 represents a hydrofluoric acid etched exhaust sensor which was subsequently electrically treated, while line 302 represents an electrode sensor which was hydrofluoric acid etched followed by electrical treatment of the electrode assembly, and line 301 represents an exhaust sensor in which the electrode assembly was electrically treated and then hydrofluoric acid etched. As is clear from the graph, the exhaust sensors of the present invention, represented by lines 301, 302 and 303 had useful response times and lower operating temperatures than other sensors: 301 and 302 were switching at 9.5 volts (an operating temperature of approximately 350 to 400° C.), with response times of about 35 milliseconds and 55 milliseconds without degrading other sensor performance characteristics, respectively, versus the other sensors which did not switch at all.

Although the electrode assembly can be first chemically treated and then electrically treated, a process of electrically treating followed by chemical etching is preferred since it produces somewhat superior results as is evident from FIGS. 3, 5 and 6 (described below).

Chemical treatment is believed to remove contaminants from the surface of the etched electrode(s), particularly silicon compounds, such as silica, and/or aluminum compounds, such as alumina. Chemically etching comprises exposing the electrode to an etchant for a sufficient period of time to increase the amplitude of the output signal produced by the exhaust sensor when in use, by about 50 millivolts, without degrading the sensor.

The exhaust side electrode, i.e., electrode 3 in FIG. 2, is exposed to an etchant by dipping a sufficient portion of the tip of the electrode assembly 1 in an etchant to expose at least electrode 3 to the etchant for a period of typically less than 60 seconds, with a period of about 10 seconds to about 30 seconds preferred, and a period of about 15 to about 25 seconds, especially preferred, for dipping the electrode assembly in a 1% hydrofluoric acid solution.

Possible etchants include silica etchants, such as hydrofluoric acid, bromic acid, potassium hydroxide/ethanol, and others capable of removing the contaminants from the electrode surface without degrading the structural integrity of the sensor, with hydrofluoric acid and a potassium hydroxide/ethanol mixture preferred due to the improved results obtained therewith. The potassium hydroxide/ethanol mixture can have up to about 10% volume percent (vol. %) potassium, with about 1 vol. % to about 5 vol. % potassium especially preferred.

In addition to chemical etching, it is also preferred to electrically treat the sensor, or electrode assembly. Electrically treating comprises exposing the sensor or electrolyte assembly to electricity for a sufficient period of time to lower the interface impedance, obtain a higher rich voltage, and/or decrease the lean-rich response time, without degrading other performance characteristics. The sensor, which is typically heated prior to electrical treatment to a typical operating temperature, can be exposed to an alternating voltage of up to about 2 volts, with about 1.2 volts to about 1.5 volts preferred, for a period of up to about 15 seconds per exposure, with about 5 seconds to about 10 seconds per exposure preferred, for a total period of up to about 60 minutes, with about 5 to about 30 minutes preferred. The temperature for the electrical treatment is preferably about 600° C. to about 800° C., with about 700° C. especially preferred. For example, after the electrode assembly of FIG. 2 was connected to an electrical source and heated to about 700° C., a typical operating environment within an automobile, a voltage of 1.5 volts was applied to the sensor for about 5 seconds. The polarity was then reversed and a voltage of −1.5 volts was applied for about 5 seconds. This process continued for about 5 minutes. The interface impedance of the resulting sensor was then tested and compared to an untreated, conventional sensor. The electrically treated sensor revealed an order of magnitude improvement. The conventional sensor produced an impedance of about 2,000 ohms. at 700° C., while the treated sensor had an interface impedance of below 300 ohms at 700° C.

Figure 4:
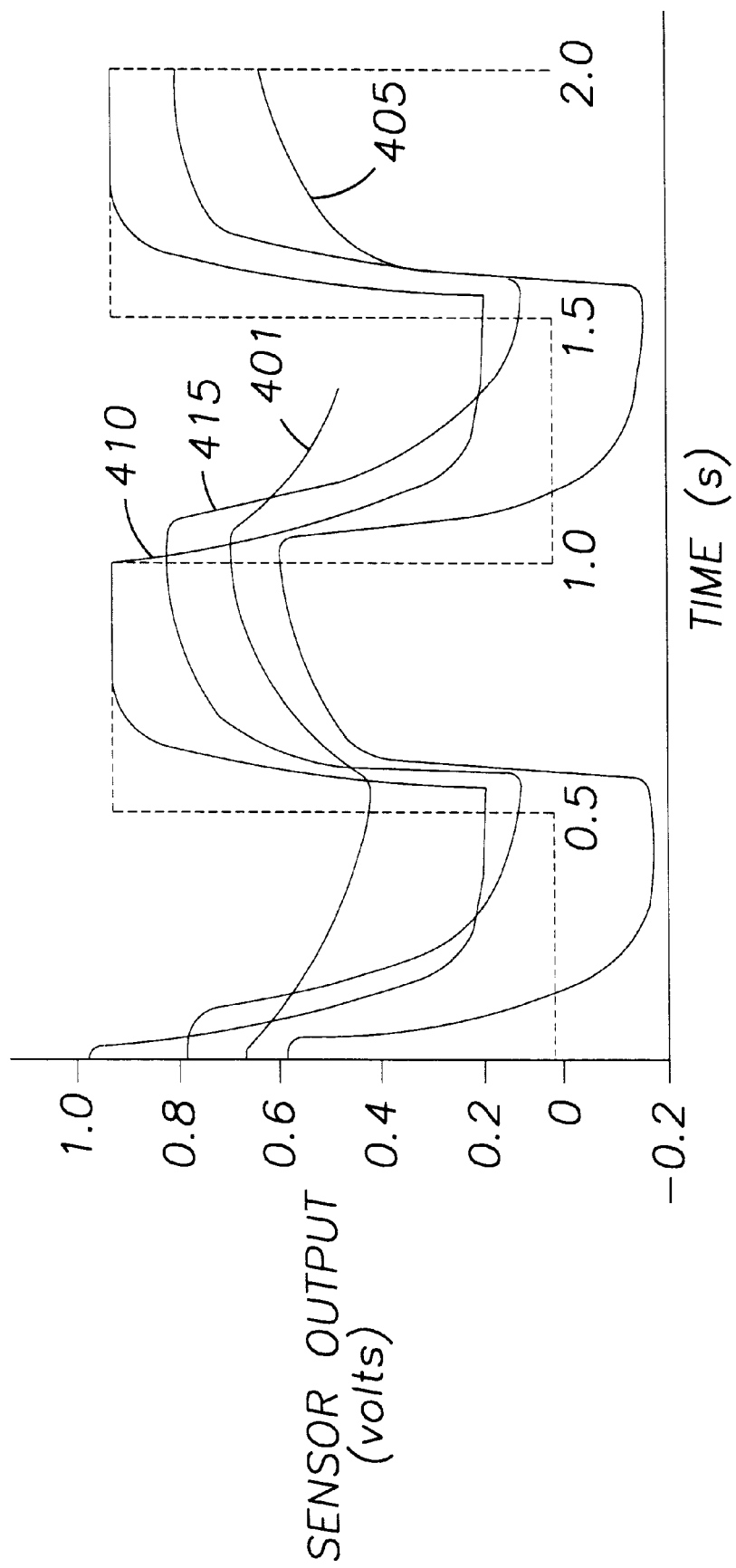
FIG. 4 is a graphic illustration of sensor output for an untreated sensor, a hydrofluoric acid etched sensor, and a hydrofluoric acid etched/electrically treated sensor, over time.

Referring to FIG. 4, the sensor output of a conventional, untreated exhaust sensor (line 401) is compared to a sensor having a hydrofluoric acid etched electrode (line 405), a sensor having a hydrofluoric acid etched electrode and electrically treated electrode assembly (line 410), and a sensor having a potassium hydroxide/ethanol etched electrode (line 415), over time. As can be seen from this illustration, the hydrofluoric acid etched and potassium hydroxide/ethanol etched sensors had a significantly higher amplitude (both over 600 millivolts) versus the conventional sensor (less than 300 millivolts). The hydrofluoric acid etched sensor (line 405), however, produced a negative signal of about −200 millivolts, which can cause a false leakage reading during operation. The sensor having a hydrofluoric acid etched electrode and electrically treated electrode assembly (line 410), however, had significantly improved amplitude while only producing positive readings.

Figure 5:
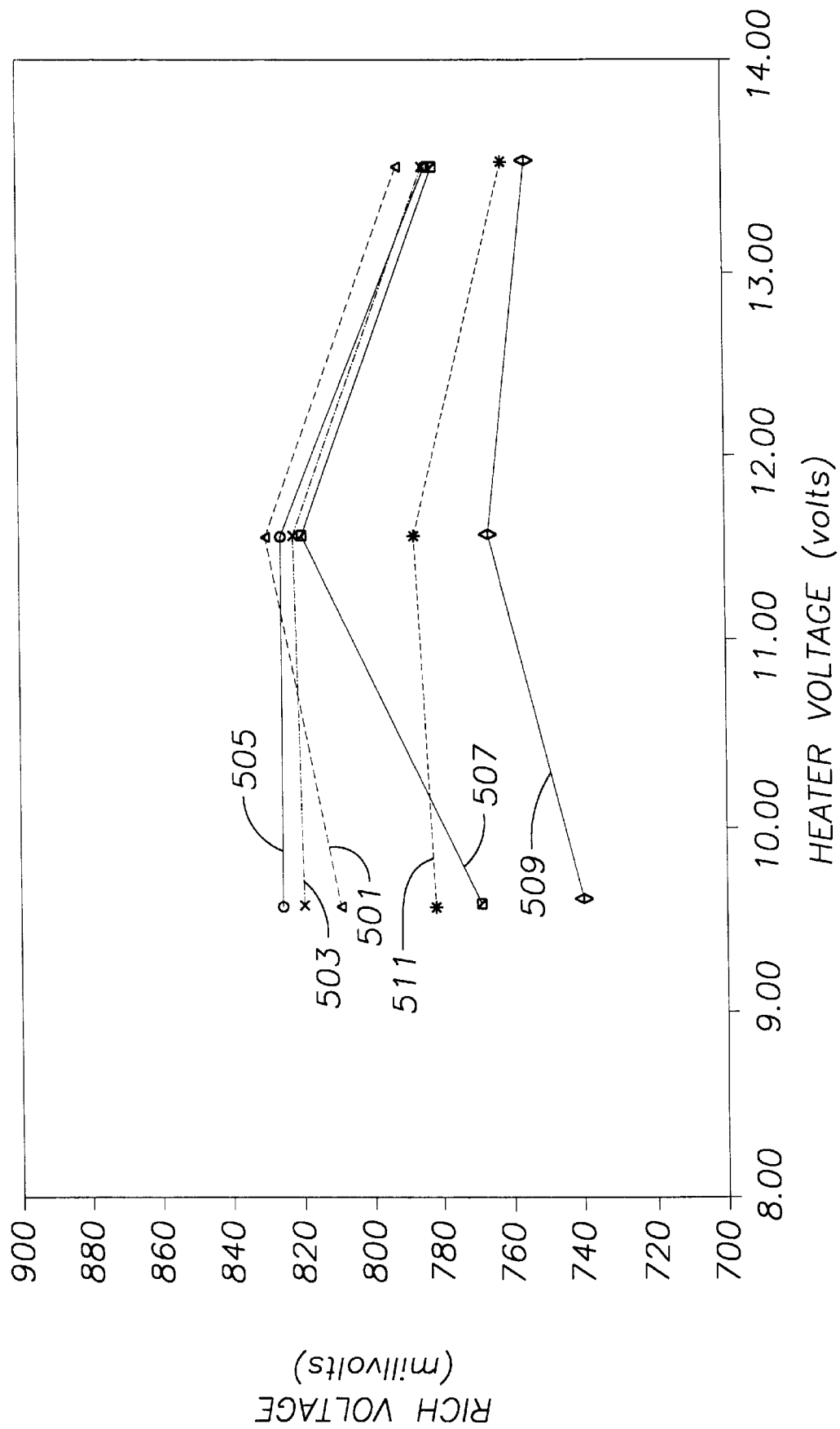
FIG. 5 is a graphic illustration of rich voltage for a sensor with a hydrofluoric acid etched electrode, a sensor having a hydrofluoric acid etched electrode and electrically treated electrode assembly, sensor with an electrically treated electrode assembly and a hydrofluoric acid etched electrode, a sensor with a hydrofluoric acid etched electrode and electrically treated sensor, an electrically treated electrode assembly, and an electrically treated sensor, with respect to heater voltage.
Figure 6:
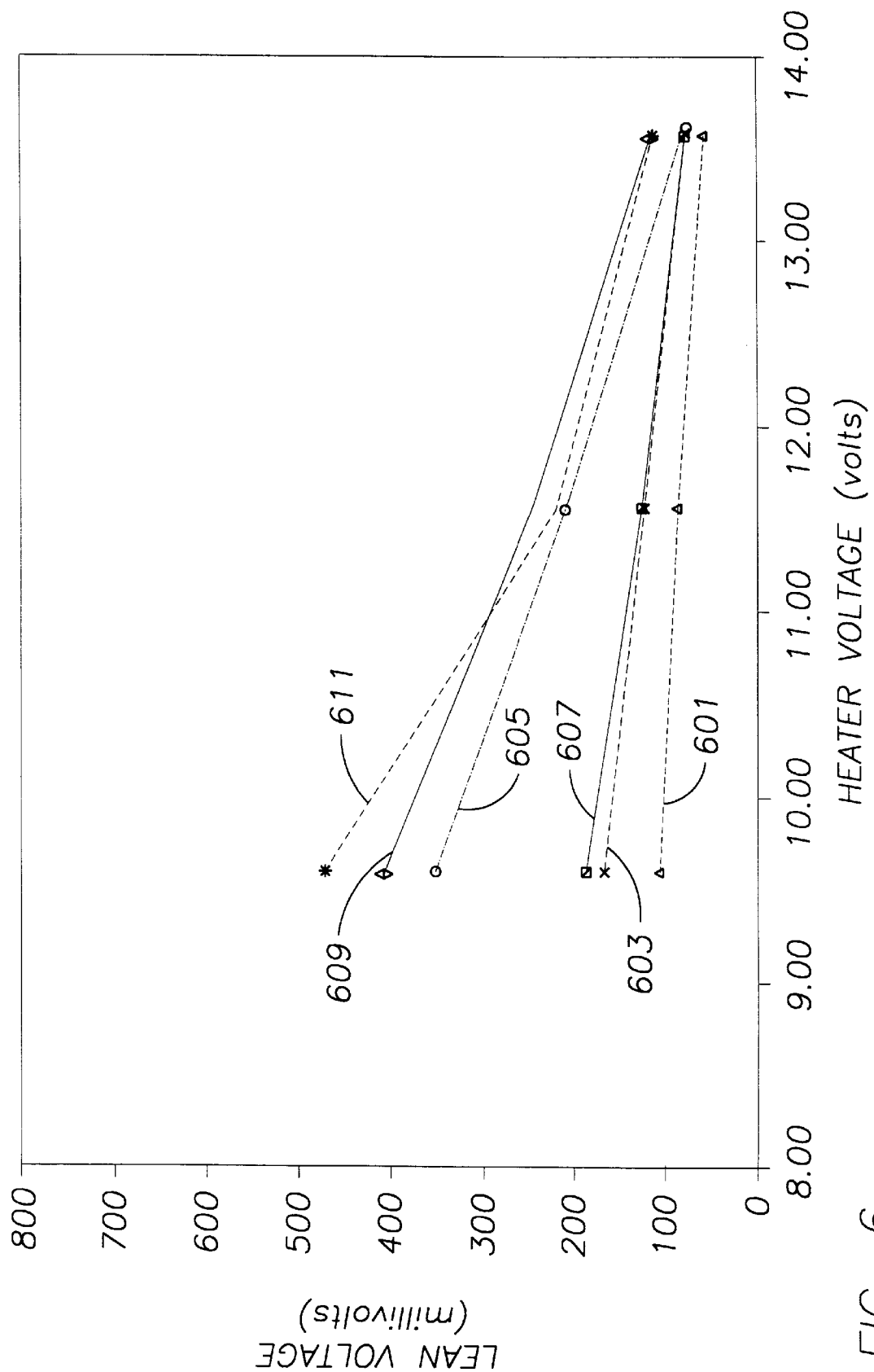
FIG. 6 is a graphic illustration of lean voltage for a sensor with a hydrofluoric acid etched electrode, a sensor having a hydrofluoric acid etched electrode and electrically treated electrode assembly, sensor with an electrically treated electrode assembly and a hydrofluoric acid etched electrode, a sensor with a hydrofluoric acid etched electrode and electrically treated sensor, an electrically treated electrode assembly, and an electrically treated sensor, with respect to heater voltage.

FIGS. 5 and 6 graphically represent the comparison of a sensor having an electrically treated electrode assembly and a hydrofluoric acid etched electrode (lines 501, 601), a sensor having a hydrofluoric acid etched electrode and electrically treated electrode assembly (lines 503, 603), an electrically treated sensor having a hydrofluoric acid etched electrode (lines 505, 605), a sensor having a hydrofluoric acid etched electrode (lines 507, 607), and a sensor having an electrically treated electrode assembly (lines 509, 609) versus an electrically treated electrode sensor (lines 511, 611) for lean voltage and rich voltage, respectively. Under both conditions, the sensor having an electrically treated electrode assembly and a hydrofluoric acid etched electrode (lines 501, 601) and the sensor having a hydrofluoric acid etched electrode and electrically treated electrode assembly (lines 503, 603) produced superior results, low reading at lean voltage and high readings at rich voltage.

EXAMPLE 1

The following example has been used to produce a sensor having an electrically treated electrode assembly and a hydrofluoric acid etched electrode.

The heater of a laminated, sintered electrode assembly, as shown in FIG. 2, was attached to a power supply, while the electrodes were attached to a second power supply. A voltage of 13.5 volts was applied to the heater to raise the temperature of the electrode assembly to about 750° C. After about 1 minute a square wave was applied to the electrodes; 1.5 volts for 5 seconds, followed by −1.5 volts for 5 seconds, for a total of 5 minutes.

The anode electrode of the electrically treated electrode assembly was then dipped in a 1% hydrofluoric acid solution for 15 seconds. The electrode assembly was then rinsed three times with deionized water to remove the hydrofluoric acid. The resulting sensor is illustrated in FIGS. 5 and 6, lines 501, 601, respectively.

EXAMPLE 2

The following example has been used to produce a sensor having a potassium hydroxide/ethanol mixture etched electrode.

The exhaust electrode of a laminated, sintered electrode assembly, as shown in FIG. 2, was dipped in a potassium hydroxide solution diluted with 50 volume percent (vol. %) ethanol for a period of 12 hours. The electrode assembly was then rinsed three times with deionized water to remove the potassium hydroxide/ethanol mixture. The resulting sensor is illustrated in FIG. 4, line 415.

As is well known in the art, exhaust sensors provide important feed back regarding the engine efficiency. Prompt, accurate information is very useful in improving the efficiency and performance of a vehicle. The exhaust sensor of the present invention has improved accuracy, reliability, and reproducibility, possibly higher manufacturing tolerances, eliminates the "green effect", enables lower operating temperatures, and substantially reduced response delay, i.e., a reduction from about 80 milliseconds of the prior art to about 20 milliseconds of the present invention (at the conventional operating temperature of about 750° C.). Note the green effect is the effect of the sensor characteristics improving after a period of use. For example, a sensor used in an automobile operates more efficiently after about 50 hours of use than when it is new. The sensors of the present invention do not experience this "green effect". They operate essentially the same, efficiently, at installation and 50 hours thereafter.

While preferred embodiments have been shown and described, various modifications and substitutions may be made thereto without departing from the spirit and scope of the invention. Accordingly, it is to be understood that the present invention has been described by way of illustrations and not limitation.

We claim:

1. A method for producing an oxygen sensor, comprising:
    disposing anode and cathode electrodes on opposite sides of a solid electrolyte to form an electrode assembly;
    electrically treating said electrode assembly with an alternating voltage; and
    chemically treating at least one of said electrodes.

2. A method as in claim 1, wherein said alternating voltage is applied in up to about 10 second intervals for a period of up to about 60 minutes.

3. A method as in claim 1, wherein said alternating voltage is up to about 2 volts alternated with a voltage of down to about −2 volts.

4. A method as in claim 3, wherein said alternating voltage is about 1.2 to about 1.5 volts alternated with a voltage of about −1.2 to about −1.5 volts.

5. A method as in claim 1, wherein said electrode assembly has an interface impedance and said electrode assembly is electrically treated for a sufficient period to reduce said interface impedance to below about 300 ohms.

6. A method as in claim 1, wherein chemically treating comprises exposing said at least one electrode to an acidic solution for a sufficient period of time to remove at least one of silicon compounds and aluminum compounds from at least one surface of said electrode.

7. A method as in claim 1, wherein said at least one electrode is chemically treated with a potassium hydroxide/ethanol mixture.

8. A method as in claim 1, wherein said at least one electrode is chemically treated with bromic acid.

9. A method as in claim 1, wherein said at least one electrode is chemically treated with hydrofluoric acid.

10. A method as in claim 1, further comprising:
    disposing said electrode assembly within a housing; and
    using a glass seal to isolate said cathode electrode from said anode electrode.

11. A method as in claim 1, wherein said electrode assembly is electrically treated and subsequently said at least one electrode is chemically treated.

12. A method for producing an oxygen sensor, comprising:
    disposing anode and cathode electrodes on opposite sides of a solid electrolyte to form an electrode assembly; and
    chemically treating at least one of said electrodes with a potassium hydroxide/ethanol mixture.

* * * * *